(12) United States Patent
Dzenis

(10) Patent No.: US 11,333,654 B1
(45) Date of Patent: *May 17, 2022

(54) GREENHOUSE GAS EMISSION REDUCTION VIA METHODS FOR REDUCING STANDARD VARIATION IN PRODUCTION OF VISCOUS MIXTURES OR SUBSTANCES

(71) Applicant: Gunars Dzenis, Peachtree City, GA (US)

(72) Inventor: Gunars Dzenis, Peachtree City, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,324

(22) Filed: May 12, 2020

Related U.S. Application Data

(63) Continuation-in-part of application No. 16/569,396, filed on Sep. 12, 2019, now Pat. No. 11,061,012.

(51) Int. Cl.
*G01N 33/38* (2006.01)
*G01K 7/00* (2006.01)

(52) U.S. Cl.
CPC ............. *G01N 33/383* (2013.01); *G01K 7/00* (2013.01)

(58) Field of Classification Search
CPC ...... G01N 33/383; G01N 19/00; G01N 25/58; G06K 7/10158; G06K 7/10128; H04W 4/80; G01K 7/00
USPC .................. 340/10.1–10.5; 700/265; 366/59; 706/12
See application file for complete search history.

(56) References Cited

U.S. PATENT DOCUMENTS

| | | | | |
|---|---|---|---|---|
| 5,541,855 A | * | 7/1996 | Enzler ..................... | G01N 11/14 366/142 |
| 6,045,730 A | * | 4/2000 | Potter ..................... | B28B 11/24 156/346 |
| 6,779,385 B2 | * | 8/2004 | Belanger ............ | G01N 33/2847 73/73 |
| 7,289,916 B2 | * | 10/2007 | Drnevich ................ | C04B 28/02 702/138 |
| 7,384,180 B2 | * | 6/2008 | Jarvinen .............. | G01N 33/383 366/2 |
| 7,457,785 B1 | * | 11/2008 | Greitzer ................... | G01D 1/18 706/12 |

(Continued)

*Primary Examiner* — Nam V Nguyen
(74) *Attorney, Agent, or Firm* — Michael J. Bootcheck, LLC; Michael J. Bootcheck

(57) ABSTRACT

The present invention relates to methods of greenhouse gas emission reduction by utilizing methods of the present invention in the production of viscous mixtures by determining the relative ratios or percentages of certain characteristics or properties of viscous substances, wherein temperature and/or moisture content is a key determinant. The methods may utilize placement of passive Radio Frequency Identification (RFID) instrumentation into a slurry or existing viscous mixture of substances. The RFID then reads moisture and/or other physical properties of the substance, typically process parameters such as temperature and/or pH. The readings are queried using an interrogator to acquire the data wirelessly. As a planning step, it is necessary to correlate the data with a variety of specially-developed algorithms specific to a viscous mixture associated with a particular process. The acquired readings will then provide a user with instantaneous information which will be determinative of the degree of completeness or maintenance of a certain property of the process.

11 Claims, 9 Drawing Sheets

(56) References Cited

U.S. PATENT DOCUMENTS

| | | | | |
|---|---|---|---|---|
| 8,818,561 | B2* | 8/2014 | Koehler | G01N 11/00 700/265 |
| 9,511,510 | B2* | 12/2016 | Roy | B28C 7/02 |
| 9,964,942 | B2* | 5/2018 | Nelson | G05B 19/402 |
| 2001/0017053 | A1* | 8/2001 | Rynhart | G01N 27/223 73/73 |
| 2017/0248475 | A1* | 8/2017 | Bonifas | G01N 25/18 |

* cited by examiner

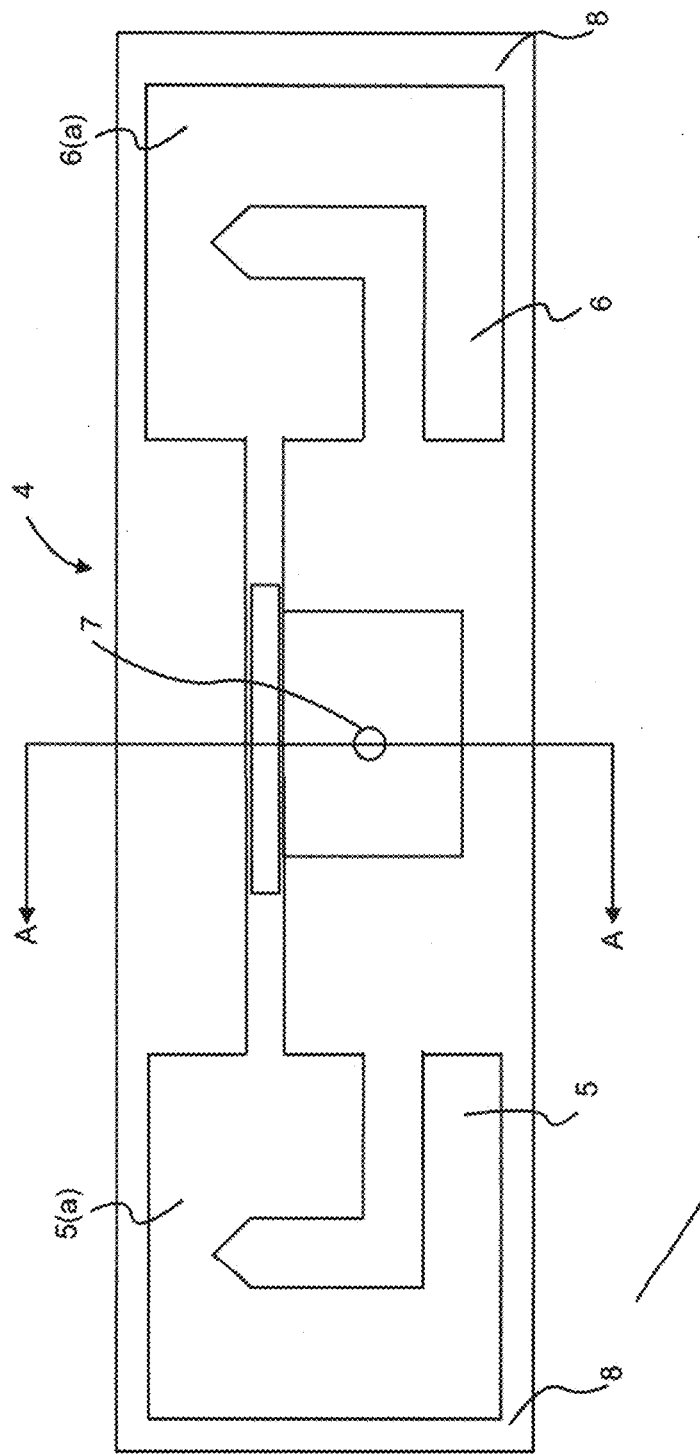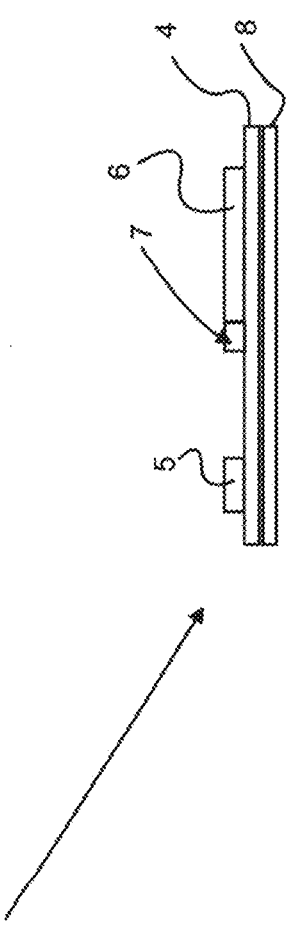

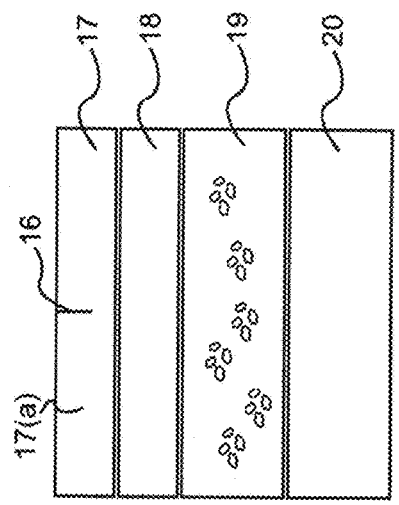
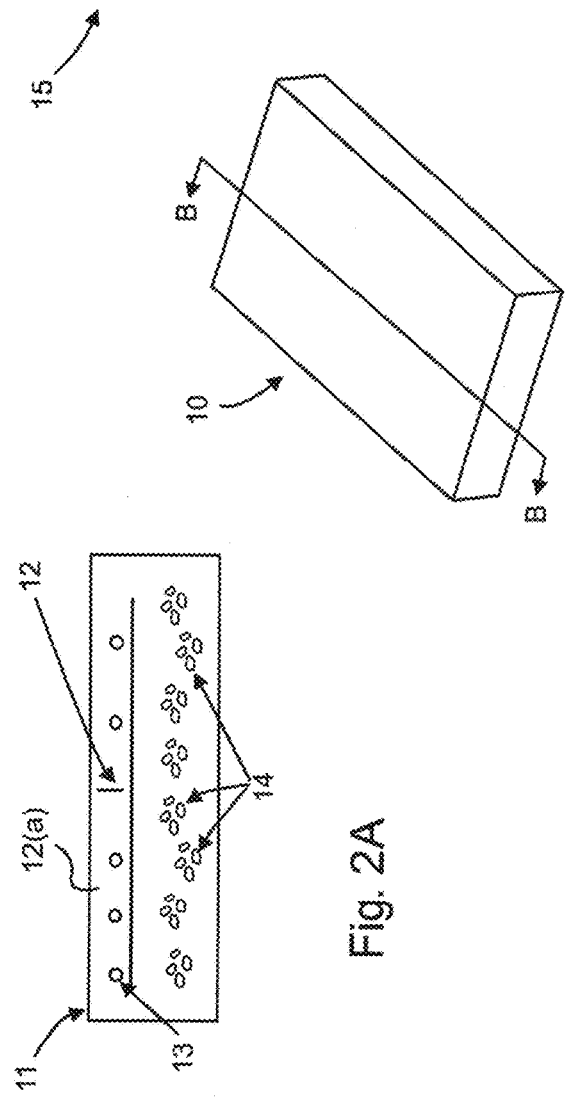
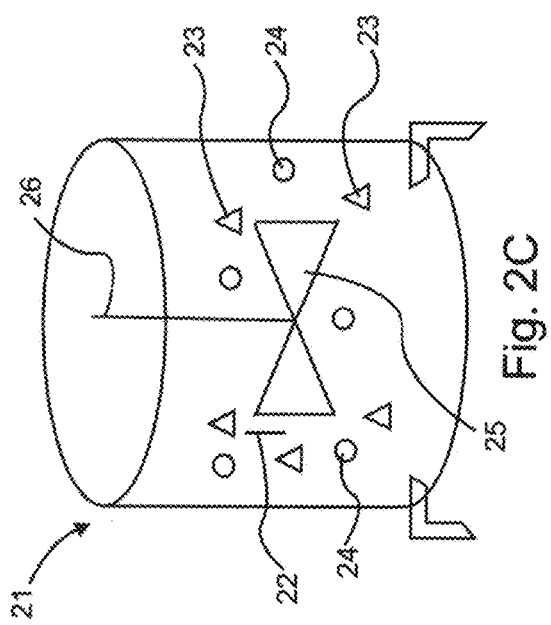
Fig. 2A
Fig. 2
Fig. 2B
Fig. 2C

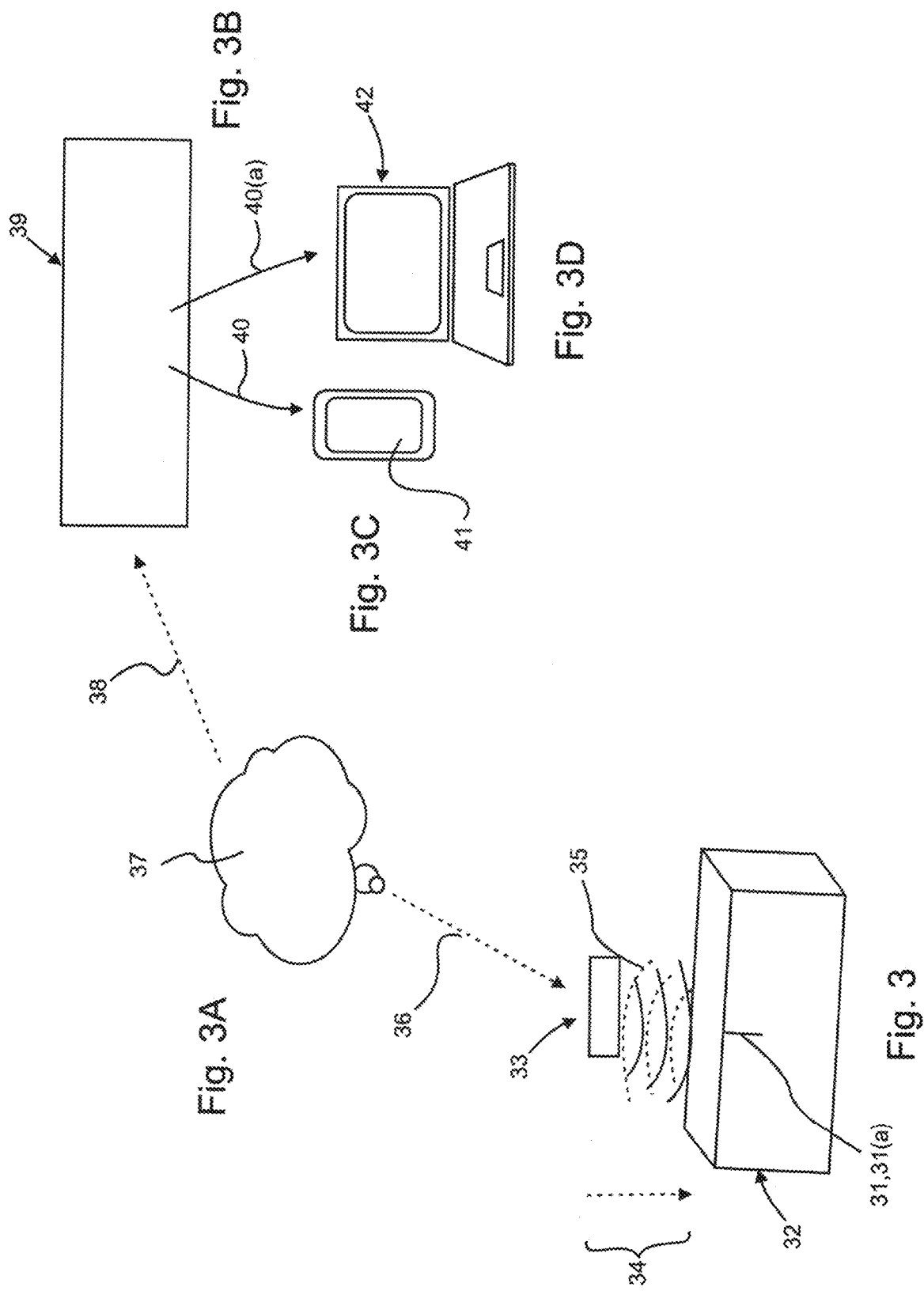

Figure 4 – Algoritm

| Cylinder Testing | | | | | |
|---|---|---|---|---|---|
| PSI AVG | StDev | StDev % of Avg | | | |
| 7624.7 | 415.7 | 5.5% | | | |
| 7910.0 | 334.8 | 4.2% | | | |
| | | | | | |
| Sensor Testing | | | | | |
| Temp AVG degF | StDev | | | StDev Reduction from Cylinders | |
| 74.1 | 1.6 | 2.2% | | 59% | |
| 61.6 | 0.7 | 1.2% | | 79% | |
| 67.63 | 0.41 | 0.6% | | 89% | |
| 67.83 | 0.31 | 0.5% | | 92% | |
| 61.59 | 0.72 | 1.2% | | 79% | |
| 61.59 | 0.72 | 1.2% | | 79% | |
| 77.71 | 1.12 | 1.4% | | 74% | |
| 77.71 | 1.12 | 1.4% | | 74% | |

Fig. 7

Effect of cement content on compressive strength at 28 days for various maximum sizes of aggregate in different types of concrete.

GREENHOUSE GAS EMISSION REDUCTION VIA METHODS FOR REDUCING STANDARD VARIATION IN PRODUCTION OF VISCOUS MIXTURES OR SUBSTANCES

CROSS-REFERENCE TO RELATED APPLICATIONS

This application claims priority from co-pending U.S. Non-Provisional application Ser. No. 16/569,396 filed 12 Sep. 2019, which is titled "Method for Determining Quality of Evolvement of a Physical Property of a Viscous Substance", which is hereby incorporated in its entirety by reference.

FIELD OF THE INVENTION

The present invention relates to methods for reducing environmental impact via viscous substance preparation by optimizing the amount of various ingredients utilized in the preparation of the viscous substance. More particularly, the invention relates to methods for reducing the amount of greenhouse gases produced in the production of concrete without sacrificing quality by reducing the amount of cement required in the preparation by more narrowly determining the amount of cement utilized.

BACKGROUND OF THE INVENTION

The production of various viscous substances, including concrete, involves the mixing of air and three basic components: water, aggregate (most commonly, rock, sand, or gravel), and a binding agent (namely Portland cement in the production/preparation of concrete). The cement is by far the most expensive component and is commonly utilized in a powder form and is a binding agent when mixed with water and aggregates. Typical concrete consists of up to 8% air (by volume), 7-15% cement, 14-21% water and 60-75% aggregate (coarse and fine).

The central key of achieving a strong, durable concrete lies in the accurate proportioning and mixing of the ingredients. This will involve the curing, reactivity, maintenance, or transport of a viscous mixture, such as concrete, asphalt, and other types of materials which at some point, exist in a slurry condition.

As mentioned above, there are many processes in which the control of moisture content plays an important variable. In most cases, it is difficult or very expensive to measure the moisture content and therefore it is rarely done. As a substantial improvement to these processes, the method disclosed herein effectively and accurately measures certain physical properties of the viscous substance, including, but not limited to, temperature, moisture content, density, specific gravity, thermal conductivity, electrical conductivity, hardness, strength, and ductility.

By way of further example, concrete production involves reacting several ingredients, to include water, aggregate, cement, and other additives. The concrete is made as a viscous fluid, placed into a form to provide a desired shape, and then the exothermic process is allowed to occur. During the exothermic process, temperature and moisture content play a key role in the proper curing process to develop the desired compressive strength. Current methods of determining the cure rate of concrete have associated concerns, as will be described.

The most common method of determining whether concrete is ready at full strength, involves using standard best practice methods of waiting 28 days, regardless of actual product or environmental conditions. The 28 day wait time method is simply an accepted industry best practices and is not based on actual performance of the concrete in question.

Another method of assessing concrete readiness involves obtaining cylinders of the concrete mix in question and testing each cylindrical sample. This required getting several cylinders and filling them with concrete from same batch. These cylinders are then tested periodically until two cylinders produce the minimum desired compressive strength. The cylinders are only an approximation of the curing of the concrete since they are lab tested and do not exist under the same conditions of the actual concrete project in question.

In prior art methods, determining the cured state of concrete also may be assessed using battery sensors embedded in the concrete. These sensors are typically calibrated to measure temperature. The battery sensors are comparatively expensive and have a limited temperature tolerance and lifespan. Battery operated sensors are also bulky and need to be embedded in the concrete, which takes a lot of space, and there is also some concern with how the embedded batteries will impact the strength of the concrete.

Another method that is sometimes applied for determining the strength of concrete is by the use of concrete temperature and/or moisture meters/sensors. However, these concrete moisture meters only measure the surface moisture content. Since a particular concrete structure could be feet, not inches, deep, measuring only the surface moisture content is not practical or safe in applications in which a sealant or other building material will be installed over the concrete. Similarly, temperature sensors can reveal valuable information about the status/condition of the concrete.

The surface of the concrete may be bone-dry, but deeper in the concrete form substantial amounts of water may still be present that will need to be released to ensure the strength of the finished product.

Asphalt-laid surfaces frequently show distress which is caused by both movement of traffic over the surface and moisture in the asphalt. The quality of the asphalt mixes, measured by its density, is an important factor to ensure the integrity of the pavement. An improper amount of moisture in an asphalt mixture reduces the asphalt-aggregate bond, which leads to the degradation of the final asphalt product. One possible consequence is what is termed a "tender mix." A tender mix is an internally unstable mix that tends to displace laterally and shove rather than compact under roller loads. Internal mix stability is a function of asphalt binder viscosity and aggregate gradation and shape. Unfortunately, asphalt technologists consider the accurate determination of moisture in an asphalt mixture to be a difficult prospect.

Another industrial process in which moisture is important is that of chemical reactions in which only a small, but precise, amount of water is needed. For example, Diels-Alder reactions work well with a minimal amount of water to neat reactants. In addition, the presence of water will result in an increased reaction rate and formation of a higher purity product. A way to measure moisture content as a large scale process would be valuable. The same is true for all reaction processes that consume water or release water as a by-product.

Production/preparation of concrete is also one of the largest producers of Carbon Dioxide ($CO_2$) and therefore greenhouse gases. $CO_2$ emission from concrete production is directly proportional to the cement in the concrete mix; 900 kg of $CO_2$ are emitted for the fabrication of every ton of cement, accounting for 88% of the emissions associated with the average concrete mix.

The compressive strength of concrete is the most common performance attribute used by engineers and mix designers. Compressive strength is measured by breaking cylindrical concrete specimens in a compression testing machine. A standard deviation of between +/−500 pounds per square inch ("psi") is acceptable if the mix design is <5000 psi according to generally accepted standards. If the mix design is >5000 psi, then 10% standard deviation is acceptable. Herein, a standard deviation in concrete mix design is also referred to as a margin of safety requirement. Margin of safety requirements based on prior art methodologies, such as the ten percent guidelines are referred to herein as a standard margin of safety requirement. Such standard margin of safety requirement may also be based on other percentages or guidelines. In determining an improved standard deviation according to the present invention, a new, i.e., improved standard deviation is produced and results in an improved margin of safety requirement.

In statistics the empirical rule states that to have 99.7% confidence, the data needs to be +/−3 standard deviations from the mean. If the engineers and designers plan to have a 5000 psi mix and the acceptable standard deviation is 500 psi, then the bell curve would have a minimum of 3500 psi, a mean of 5000 psi and a maximum of 6500 psi to have a 99.7% confidence. However, if the expected design mix is 5000 psi, then it would be unacceptable to have a result that is less than 5000 psi. Therefore, mix designers must over-engineer their mix to make sure the concrete is not below expected psi. If the standard deviation is 500 psi and the desired strength is 5000 psi, and never less, then the actual mix design must be 6500 psi. The minimum expected is 5000 psi (3x−500 psi), the mean is 6500 psi and the maximum expected is 8000 psi (3x+500 psi). Because the standard deviation of cylinder test results is high, in order to have 99.7% confidence the mix design is not less than 5000 psi, mix designers must over design the mix to 6500 psi.

The method of giving more strength to a concrete mix is to increase the amount of cement, which is also the most expensive part of the design mix. Cement is also the highest contributor to greenhouse gas emissions. Due to the high accepted standard deviation, there is a high financial cost of overengineering and a high environmental cost. Historically, there hasn't been an effective and safe way to reduce the standard deviation, which would lower the cost of concrete to society, suppliers and end users as well as reduce the greenhouse gas emissions to the benefit of society and the environment.

There is a need for an inexpensive device and method that, in the context of conducting a particular process, can measure moisture content and/or temperature (or other parameter/characteristic/condition) within a viscous mixture in a non-destructive and safe manner. This device should be easy to use so as to provide instant, accurate information on the moisture content, temperature, and/or other parameters/characteristics/conditions of the fluid which is utilized in the process. The device ideally will have a long lifespan and capable of withstanding high temperatures. This device should be small and unobtrusive and measure moisture content and/or temperatures (or other parameter/characteristic/condition). This market need is not only for the concrete and asphalt industries, but other commercial or manufacturing endeavors. The foregoing examples were presented for illustrative purposes only, and do not serve to limit the applicability of the devices and methods disclosed in this document.

SUMMARY OF THE INVENTION

It is to be understood that both the foregoing general description and the following detailed description present methods and processes of the invention, and are intended to provide an overview, or framework, for understanding the nature and character of the invention as it is claimed. The accompanying drawings are included to provide a further understanding of the invention, and are incorporated into and constitute part of this specification. The drawings illustrate various embodiments of the invention and, together with the description serve to explain the principles and operations of the invention.

The inventive concept discloses a method of reducing production of greenhouse gases by utilizing a process whereby the progress of curing, state of desired hardening, relative viscosity, or maintenance of substance proportions of the internal mass of a viscous substance can be determined and measured electronically at any stage of a specific process to more accurately assess the qualities of the substance. In differing embodiments, the disclosed method measures certain physical properties of the viscous substance, including, but not limited to, temperature, moisture content, density, specific gravity, pH, thermal conductivity, electrical conductivity, hardness, strength, and ductility.

In some embodiments, the method provides at least one small, passive Radio-Frequency Identification (RFID) sensing device that measures moisture, temperature, pH, and/or other parameters of a viscous fluid mixture associated with the various phases of an industrial or manufacturing process. The specific viscous fluid may or may not, undergo gradual change during its maturation into the desired ultimate product. In one embodiment, this inventive concept is intended to monitor curing or drying processes. In such uses, the passive sensing device, (for example, a concrete sensor 12, or a chemical sensor 22) must be embedded within the subject fluid so as to provide ongoing, accurate measurements.

A variety of sensors may be placed at different locations, or utilized for various applications, during a specific process. Each individual sensor is designated with a unique identification code or "tag." The sensor tag 4 would be rewritable and be able to provide key data concerning the pertinent process, such as date, time and/or location of creation, or date of expiration, current location of tag (such as GPS location), etc.

Whenever the sensor is read, the key information is immediately displayed. In some embodiments, the operating temperature range of the sensor must be functional from below freezing to above boiling. An interrogator 33 is used to read and wirelessly transmit the moisture content, temperature, and/or pH data given by the sensor 12, 22. The interrogator 33 sends the data to a specific software application or other program which will be populated with the algorithm(s). This data will then be converted to a useable format. Temperature sensors may be utilized in one or more embodiments. Similarly, moisture content, pH, density and other sensors may be utilized either independently or in conjunction with temperature sensors. In some embodiments, temperature passive RFID sensors are utilized.

In some embodiments, the sensor 12, 22 is the size of a business card (i.e., length, width, thickness, etc), however, sizes may vary, dependent upon the state of the technology used and the capabilities of the interrogator 33.

In utilizing the methods and processes above, the amount of a key ingredient, such as cement in the case of concrete production may be more accurately determined such that the amount of cement is reduced for a needed compressive strength product. By reducing the cement utilized, greenhouse gases produced in the manufacturing process is correspondingly reduced. Further, significant financial savings are realized when reducing the amount of cement utilized.

BRIEF DESCRIPTION OF THE FIGURES

FIG. 1A is a drawing of a typical sensor 4, showing the sensor pickup area 7 for measurement of a specific property of a viscous substance, along with the left and right antenna sections 5, 6;

FIG. 1B illustrates a side view 9 of the sensor 4 of FIG. 1A, as seen from the perspective of section line A-A;

FIG. 2 illustrates a stylized cutout of a block section 10 of any of a variety of specific materials, further showing the cross-sectional direction of view of the section 10;

FIG. 2A presents a cross-sectional view of a hypothetical section of concrete 11, as would be seen from section line B-B, further showing a generic sensor 12 (sensor specific to concrete) embedded within;

FIG. 2B shows a cross-sectional view of a section of asphalt 15 with a sensor 16 specific to asphalt embedded near the top surface 17. FIG. 2B further shows the asphalt base layer 18, the aggregate layer 19, and the soil sub-grade 20;

FIG. 2C presents a stylized view of the interior of a chemical mixing, or reactive, tank 21. Also shown is a sensor 22 embedded with other mix components, these components typically a first chemical agent 23, a second chemical agent 24. Stylized mixing blades, are represented by item 25;

FIG. 3 depicts the flow of the process of reading the information acquired by a tag 31(a) attached to a sensor 31 embedded within a container 32 of viscous fluid mixture. The information is garnered by an interrogator 33 and transmitted to an internet-based "Cloud" 37 data storage system;

FIG. 3A is a stylized presentation of the Cloud 37 which stores, processes, and provides access to the corresponding algorithms 38;

FIG. 3B represents the electronic consolidation 39 of a variety of algorithms and transmittal to final users;

FIG. 3C depicts a mobile phone or device 41 for reception of the algorithmic information;

FIG. 3D illustrates a desktop computer 42 for reception of the algorithmic information;

FIG. 7 presents an exemplary data set according to the present invention;

DETAILED DESCRIPTION OF THE INVENTION

Figure 4B:
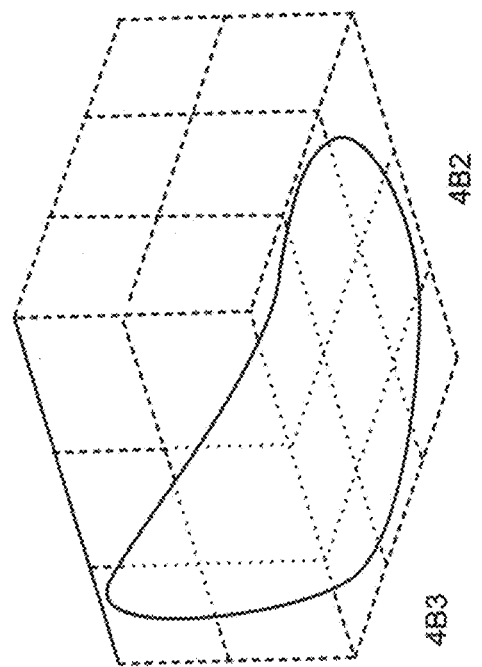
FIG. 4A and FIG. 4B show stylized, three-dimensional representations of algorithms that track the variables of temperature, moisture, and pH factor during stages of a process involved with acquiring hardness, or compressive strength, of a specific viscous fluid.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains. In the figures, like reference numbers represent the same component.

The discussion of the present inventive concept will be initiated with FIG. 1A. In FIG. 1A there is illustrated a plan view of a typical electronic sensor 4, further equipped with a "tag." The tag pickup area 7 is utilized for measurement of a specific property of a viscous fluid 40 (not shown), while the left and right antenna sections 5, 6 are shown integral to the left antenna base 5(a) and right antenna base 6(a). The tag device measures moisture, temperature, pH, or other process parameters, that would be essential to maintenance or completion of a finished product.

FIG. 1B illustrates a side view 9 of the sensor 4 and further shows an adhesive backing 8 which backing 8 normally comes as standard configuration for off-the-shelf sensors 4 of this type. The sensor 4, in conjunction with a tag, acquires information on the properties of a viscous fluid, or other substance in which the sensor 4 immersed. This information is stored electronically within the tag until electronically interrogated by a compatible device which emits interrogating radio waves. The interrogating device (not shown) is essentially a small, passive Radio Frequency Identification (RFID) emitter that may be mobile or at a stationary location. The information may also be transmitted by conventional electronic communication via a landline or similar hard-wired connection.

Temperature sensors may be utilized in one or more embodiments. Similarly, moisture content, pH, density and other sensors may be utilized either independently or in conjunction with temperature sensors. In some embodiments, temperature passive RFID sensors are utilized. In exemplary embodiment the sensor 4 is passive. Other embodiments of this inventive concept may be equipped with battery-powered, or locally-powered sensors 4. These are generally known as "active" tags and may operate at hundreds of meters from an RFID reader.

In FIG. 2 there is illustrated a hypothetical block of any of a variety of materials 10. Section line B-B, depicts the orientation of a cross-sectional view of any one of different varieties of the block material 10. FIG. 2A specifically represents a cross-sectional view of concrete block material 11. A specific concrete sensor 12, essentially functioning in the same manner as sensors 4 previously described, is embedded near the concrete outer surface 12(a).

The concrete rebar 13, along with aggregate 14 typically found in concrete structures is also shown.

In FIG. 2B there is illustrated a cross-sectional view (an approximation of the view from cross-section line B-B) of a block of asphalt 15. A specific asphalt sensor 16, along with a tag 16(a), functions in the same manner as the sensor 4 previously described. The asphalt sensor 16 is embedded near the surface 17(a) of the asphalt layer 17, directly above the asphalt base layer 18. The asphalt aggregate layer 19 and the soil subgrade 20 are further shown.

FIG. 2C depicts a stylized view of the interior of a chemical mixing, or reaction, tank 21. A sensor 22, along with its associated tag 22(a) (not shown) is embedded within chemical components, which by way of illustration only, comprise a first chemical 23 and a second chemical 24. Both chemicals 23, 24 are conceivably mixed with other necessary components.

FIG. 2C, thus depicts representations of the various constituents that may be included in a mixing/reactive tank 21. Further shown is a mixing blade 25 and a blade axis 26 integral to the reaction tank 21.

FIG. 3 depicts the process of reading the information acquired by a tag 31(a) attached to a sensor 31 embedded within a container 32 of viscous fluid mixture. The sensor 31 and its tag 31(a), when electronically prompted, picks up data from the changing parameters of the viscous fluid in which it is embedded, the data being in a readily useable form for electronic transmission. An electronic interrogator 33 either automatically, or upon manual actuation, generates electromagnetic radio waves 34 to empower the sensor's tag 31(a). Thus, the interrogator 33 provides minute amounts of power 34 to the sensor 31 and the tag 31(a) shown as FIG. 3. The sensor 31, upon receiving power from the interrogator 33, reads the current conditions of the process and has enough power to send the signal back to the interrogator 33.

The interrogator 33 then stores and sends the data wirelessly to a storage location, typically to a Cloud 37 location. In some embodiments, the current conditions of the process may be transmitted by conventional electronic communication via a land-line or similar hard-wired connections. In FIG. 3, the depicted sensor 31 functions in the same manner as described earlier for typical sensors 4 of this type, and is embedded in the container 32 of viscous fluid. The viscous fluid could be, by way of illustration, and not limitation, concrete, asphalt, chemical reactants, or other manufacturing or industrial substances. One common characteristic of such viscous fluids is that water, or moisture content, plays a key variable in any curing or manufacturing process.

The passive sensor 31 receives electrical power from the interrogator 33 and implements readings of physical properties of the viscous substance, including, but not limited to, moisture, temperature, pH or substance parameters. The sensor 31 then transmits, by radio wave 35, its readings back to the interrogator 33, shown in FIG. 3 as an arrow and broken curvilinear waves.

With the unique tag 31(a) of the sensor 31, precise readings can be correlated to the location of the sensor 31 within the viscous fluid, or perhaps the unique individual tags of multiple sensors within the fluid. The interrogator 33 may temporarily store, or transmit 36 the readings received from the sensor 31 to a cloud 37 data storage system, as shown in FIG. 3A.

The data stored in the cloud 37 is maintained and made available, accessible, and interpretable by means of various algorithms 38.

Figure 4A:
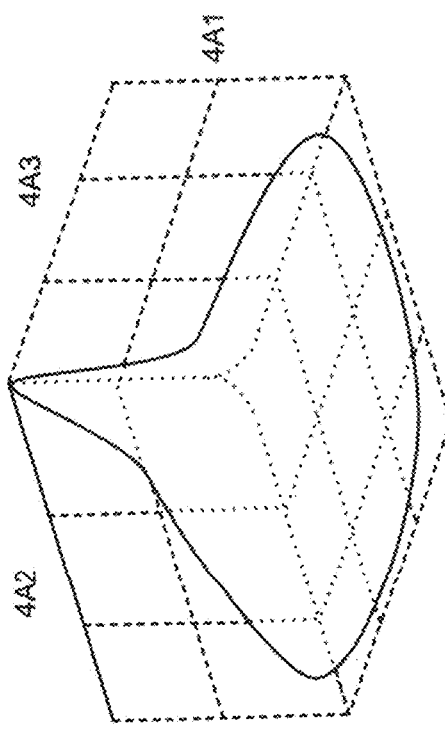

A specific algorithm or algorithms 38 translates the data given by the sensor 33 into a useable form depending on the specific process which takes place. FIG. 3B is a representation of the collection and consolidation of specific algorithm 39 generated by means of the immediately preceding examples. As is expected, for accuracy in assessing the attainment of a substance phase for specific processes, it is essential that different algorithms 38 be utilized for instance, with different grades of concrete (2000 psi, 2500 psi, 3000 psi, etc.). Further, different algorithms 38 must be computed for the differing grades of asphalt (1-2, 1-4, 1-5, etc.). It is necessary that custom-designed/calculated algorithms 38 be calculated for other specific processes. FIG. 4A and FIG. 4B provide information on the function of certain algorithms 38 for assessment of each phase or phases of completion of a process.

Once the data is collected in the Cloud 37 data storage system and the appropriate algorithm 38 translates 39 the collected data, the information is sent to a final user or users (not shown) via appropriate communications means 40 and 40(a). Ultimate end users may acquire the transmitted data 39 by means of mobile phones 41 and desktop computers 42, respectively, shown in FIG. 3C and FIG. 3D.

In FIG. 4 (comprising FIG. 4A and FIG. 4B) there is shown a three-dimensional, pictorial representations of algorithms correlating moisture, temperature, and/or pH to the relative percentage of completion of a process to achieve hardness, or compressive strength. FIG. 4A relates low moisture or low temperature or pH to a high percentage completion of the process. Percentage completion of the process is represented by 4A1, with 4A2 being moisture content, and 4A3 is temperature.

FIG. 4B relates high moisture or low temperature or pH to high percentage complete process. Item 4B1 is percentage completion of the process, 4B2 is moisture content, and 4B3 is temperature. Each application in which a sensor will be used to determine the percentage completion of the process will have its own unique algorithm developed.

A data collection period will be used for collection of results of temperature, moisture, and pH readings over specific times under varying conditions. The resultant rendering of the hardness and strength, or possibly a curing objective 97 of the substance can then be precisely indicated. All the data collected will be plotted until algorithmic graphs are created, as demonstrated with FIG. 4A and FIG. 4B. As an example, assuming concrete slurry is the substance, in FIG. 4B, all moisture readings are on the X-axis represented by axis 4B2. When there is low moisture in concrete, it is expected that the PSI strength of concrete is high. The PSI (or percentage of finished curing process) is in the Z-direction of the 3-dimensional graph, represented by axis 4B1. On the Y-Axis is temperature, represented by axis 4B3.

In FIG. 4B, the plot, "4B2" is the moisture content axis. At the far left is very low moisture and the far right is very wet. If there were presented a scale from 0.0% to 100.0% moisture, then perhaps in a concrete application, this would translate to a correlated scale of 1.0% to about 15.0% moisture. The most practical utilization of the disclosed inventive concept is to focus on the key parameters in critical ranges, for instance, 0.0% to 30.0% range instead of 0.0% to 100.0% moisture.

In FIG. 4B, "4B3" represents temperature axis. To the left is low temperature and to the right is high temperature. The temperature range, in Celsius, is between 10.0 and 35.0 degrees. The customarily-designated Z-axis 4B1 depicts the strength of concrete in PSI. Higher readings on the Z-axis 4B1 translates to higher strength while lower readings in the Z-axis 4B1 represent lower levels of strength. Basically, when the temperature is close to ambient (when concrete is poured it gets hot) and moisture content is low, the current strength of the concrete batch will be high.

Again, using concrete as the representative substance, when the temperature may be high, there is still curing time left. Only when the moisture content is low and temperature is also relatively low, will the curing of the concrete be complete. Therefore, the moisture reading and temperature, once known, can be plotted and compared to previous data to determine the third variable, the compressive strength of concrete, which would be representative of the percentage of a complete curing process of concrete. Compressive strength could be in pounds per square inch, (psi) or it could be in Newtons per square millimeter ($N/mm^2$).

Figure 5:
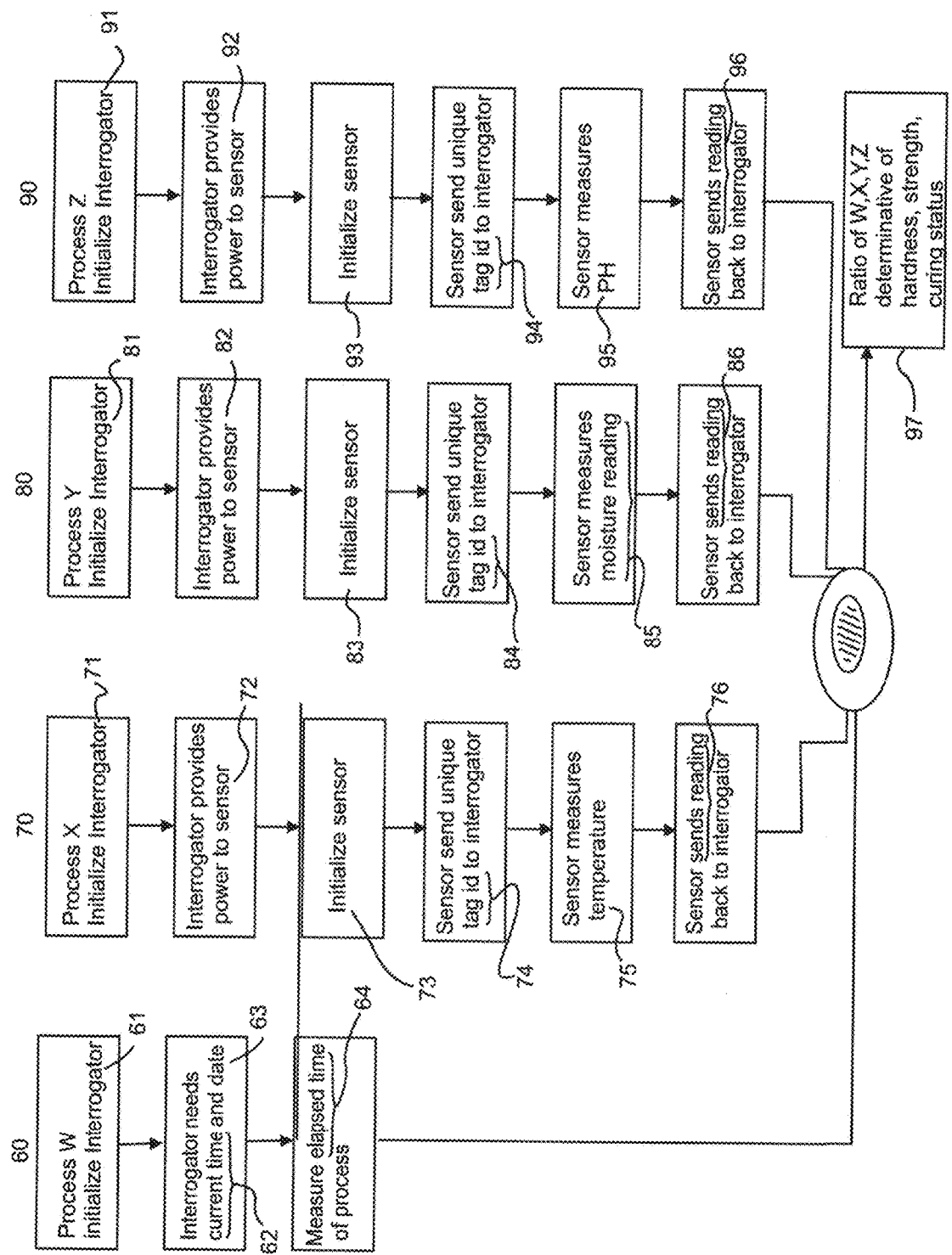
FIG. 5 presents an integrated flow chart depicting the various process steps necessary for accomplishing a desired condition of particular viscous fluid.

FIG. 5 presents an integrated flow chart depicting the various process steps 60, 70, 80, 90, necessary for accomplishing a desired condition of particular viscous fluid. At process W 60, an interrogator 61 initiates the current time 62 and date 63 and maintains a continuous tracking of elapsed time 64. At process X 70 an interrogator 71 provides power to the applicable sensor 72, which sensor 72 sends its unique tag ID 74, and its reading 76 of temperature 75 back to the interrogator 71.

At process 80 an interrogator 81 provides power to the applicable sensor 82, which sensor 82 sends both its unique tag ID 84, and the reading 86 of moisture content 85 back to the interrogator 81. At process 90 an interrogator 91 provides power to the applicable sensor 92, which sensor 92 sends its unique tag ID 94, and its reading 96 of pH 79 back to the interrogator 91.

The culmination and ratios of the above-described processes 60, 70, 80, and 90 all render a cumulative determination of the strength and hardness 97 of the viscous fluid which is being processed.

The user(s), upon the receipt of usable moisture and related data such as temperature, pH, or other parameters, can then accurately determine the stage of the process being monitored.

Over a period of time, when the appropriate stage or completion percentage 97 of a process is determined, the user can make better decisions about the specific process, without additional testing or other complicated, inefficient attempts at guessing.

As noted above, concrete is one of the largest producers of carbon dioxide ($CO_2$) and therefore greenhouse gases. The $CO_2$ emission from the concrete production is directly proportional to the cement content used in the concrete mix; 900 kg of $CO_2$ are emitted for the fabrication of every ton of cement, accounting for 88% of the emissions associated with the average concrete mix.

By utilizing the methods and sensors taught herein that measure temperature and/or moisture that have a lower standard deviation than traditional concrete cylinder testing would reduce the (1) greenhouse gas emissions, and (2) cost of concrete.

Herein, a standard deviation in concrete mix design is also referred to as a margin of safety requirement. Margin of safety requirements based on prior art methodologies, such as the ten percent guidelines are referred to herein as a standard margin of safety requirement. Such standard margin of safety requirement may also be based on other percentages or guidelines. In determining an improved standard deviation according to the present invention, a new, i.e., improved standard deviation is produced and results in an improved margin of safety requirement.

There are approved standards, such as the Maturity Method, that allow the use of temperature sensors to approximate the early strength of concrete. The sensors could be probes, or other kind of sensors such as RFID tags. The RFID tags could be active or passive. In testing of passive RFID temperature sensors, the average standard deviation 1.5% (i.e., the improved standard deviation, and, thus, an improved margin of safety requirement). The current accepted standard deviation is 10% of the cylinder breaks (i.e., standard margin of safety requirement), but with RFID temperature sensors at a 1.5% standard deviation (a standard deviation reduction of 85%), the greenhouse gas emissions could be reduced by proportionately (via the improved margin of safety requirement). In some embodiment examples, the greenhouse gas emissions have been shown to be cut by 14%. By reducing the standard deviation of testing of concrete, there is a reduction of greenhouse gases and savings for the industry. By way of example, in one field test with a precast concrete company, one standard mix design is supposed to be 6000 psi after 28 days. Although accepted standards allowed them to have a 600 psi standard deviation (also referred to herein as standard margin of safety), their process is controlled to a 300-500 psi standard deviation, standard margin of safety. The company cannot have a break at less than 6000 psi, or it would be considered out of specification, i.e., failure.

There are previously established Maturity Curve (ASTM C 1074) based on previous testing for the same concrete mix and same process and multiple tests.

Figure 6:
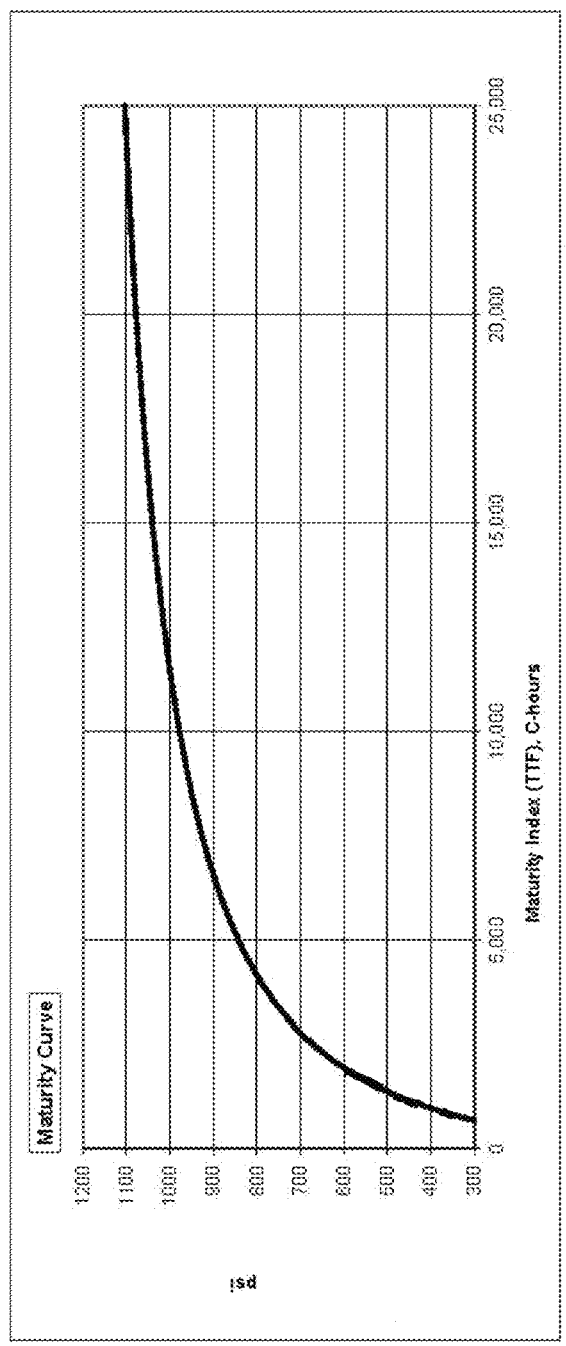
FIG. 6 presents a prior art Maturity Curve.

FIG. 6 illustrates such a Maturity Curve. On the X-axis is the Temperature-Time Factor, which is a function of Time and Temperature. On the Y-axis is the strength of concrete in psi. With multiple iterations of testing and developing a Maturity Curve, the standard deviation will be lowered.

In accordance with testing of the present invention, FIG. 7 illustrates an exemplary data set. Cylinder testing had a standard deviation of 416 and 335 psi (5.5% and 4.2% of result respectively) with 3 sample size. The average standard deviation, i.e., improved margin of safety requirement, is 375.5 or 4.85%. The sensor measuring temperature had standard deviations between 0.31 and 1.6 degrees Fahrenheit (0.6% and 2.2% respectively) with a 3 sample size. The average standard deviation is 0.8 or 1.2%. Thus, the improved margin of safety requirement is much less than the standard margin of safety requirement while still producing an acceptable concrete product.

Figure 8:
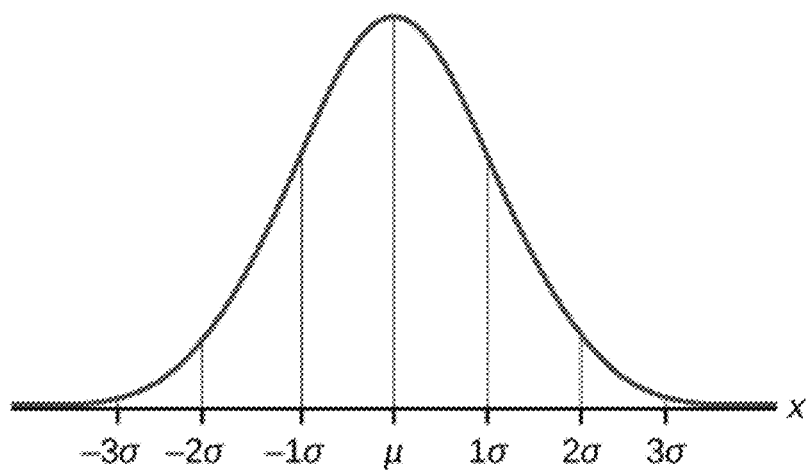
FIG. 8 illustrates a prior art statistical table.

FIG. 8 illustrates the statistical relationship of the 68-95-99.7 rule based on the number of standard deviations. To obtain 99% certainty to reach the desired breaking point, 3 standard deviations margin of error are required. Thus, Sigma ($\sigma$) of cylinder breaks=375×3=1125 psi If a 6000 psi break point is desired, then the mix design=7125 psi (6000+(375×3)).

Since the standard deviation of the temperature sensors is reduced an average of 78%, the standard deviation goes from an average of 375.5 psi to 82.6 psi.

The sigma ($\sigma$) of new cylinder breaks is thus 83×3=249 psi with the above-described method of testing the strength of concrete. The new design mix target is 6249 (6000+(249×3)) instead of 7125. This is a 12% reduction in the amount of over-designing. The net reduction of 876 psi, at a cost of +$0.01 (+/−15%) per increase of psi/Cubic yard is $8.70 per cubic yard. If a plant makes 100,000 cubic yards per year, the savings are about $870,000 per year.

Even more importantly from an environmental perspective, is the reduction in $CO_2$ concrete plant produces. In the example above, the plant produces 100,000 cubic yard of 7125 psi mix design to achieve 6000 psi. 1 CY is 1.8 Metric ton.

The $CO_2$ emission from the concrete production is directly proportional to the cement content used in the concrete mix; 900 kg of $CO_2$ are emitted for the fabrication of every ton of cement, accounting for 88% of the emissions associated with the average concrete mix.

Figure 9:
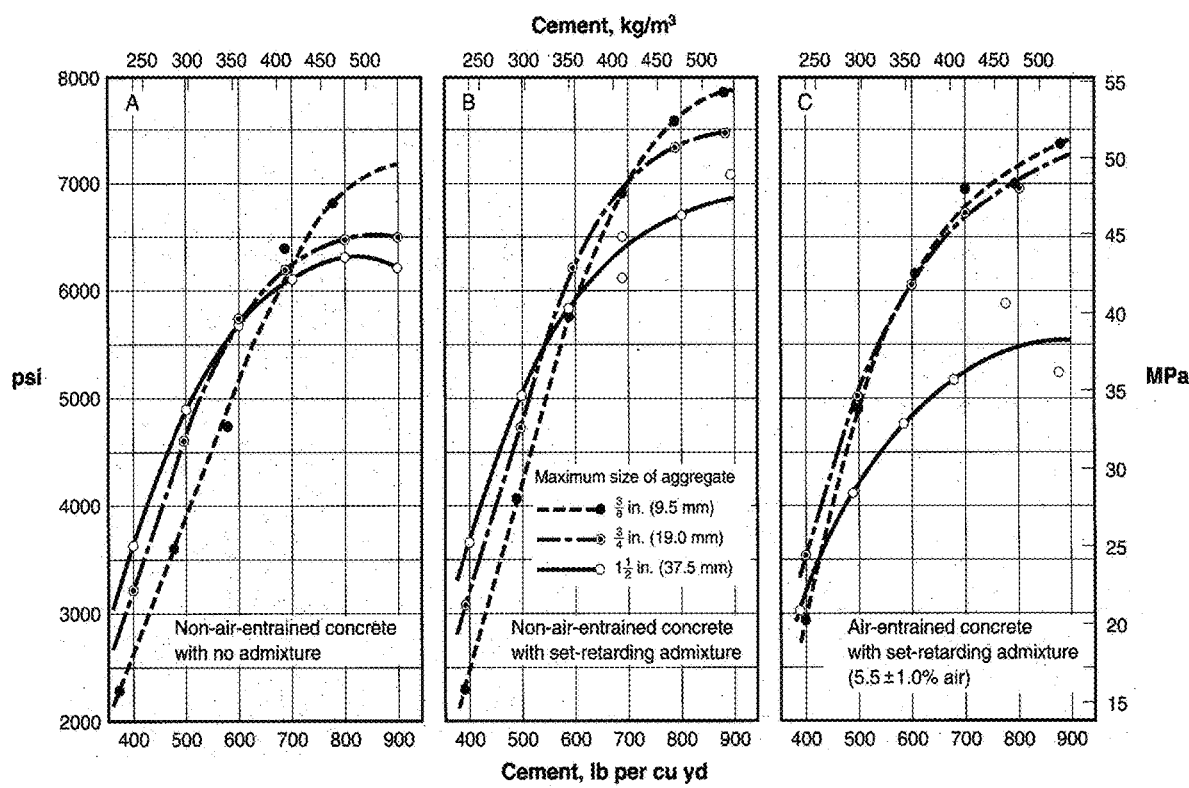
FIG. 9 illustrates a prior art cement usage chart.

FIG. 9 (https://www.cement.org/docs/default-source/th-paving-pdfs/soil_cement/eb114-high-strength-concrete.pdf) illustrates cement usage for a predetermined psi strength for a given concrete.

The amount of cement in 100 lbs. per cubic yard of concrete is approximately the psi in thousand lbs. Therefore, for a sample of 700 lbs cement per cubic yard, the strength can be estimated at 7000 psi. If a plant was previously designing a mix for 7125 psi, the plant was consuming about 712 lbs. of cement per cubic card. If the new mix design is now 6249 psi because of the utilization of the herein methods, the standard of deviation is reduced, then the plant is using 625 lbs. of cement. This resulting 12% reduction of cement usage is also reducing the carbon footprint of the plant by 12%. If the plant was making 100,000 cubic yards of concrete of 7125 psi concrete, it was consuming 712 lbs. cement/cubic yard×100,000 cubic yards=71,200,000 lbs. of cement or 32,296 metric tons of cement. 900 kg of $CO_2$ per ton of cement×32,296 metric tons=29 million kg of $CO_2$. If instead the plant is making 6249 psi mix, then it's consuming 28,350 metric tons of cement which is the equivalent of 25.5 million kg of $CO_2$. There is about a 4.5 million kgs. of $CO_2$ reduction for the plant and environment.

Thus, by reducing the amount of a key ingredient (i.e., cement in the case of concrete production, bitumen in the case of asphalt, etc.), by reducing the standard deviation necessary, a net reduction of greenhouse cases is realized. Similarly, a significant cost savings is realized through the reduction in cement utilized. Herein, reducing greenhouse gases and the cost savings realized by utilizing less cement while still meeting design parameters are two examples of benefits obtained by utilizing the presented methods and processes of the invention.

In one embodiment of the present invention; a method is presented for realizing a benefit by reducing an amount of at least one key ingredient, such as cement, by utilizing a process for determination, at any point in time, the quality or phase of a specific physical property of a viscous substance, as the substance progresses through a stages of a particular process.

In one example, the steps include (a) ascertaining a desired compressive strength requirement for a predetermined viscous substance in pounds per square inch ("psi") as a minimum required psi;

(b) calculating a standard margin of safety requirement of ten percent (though this percentage is variable) of the compressive strength requirement but wherein the standard margin of safety requirement is not less than 500 psi even if said compressive strength requirement is less than 5000 psi (this amount is similarly variable in other embodiments;

(c) ascertaining a minimum quantity of a key ingredient in the viscous substance based on a sum of the compressive strength and the standard margin of safety requirement;

(d) reviewing existing scientific tables to ascertain how much of a greenhouse gas is produced in creating a predetermined amount of the viscous substance based on the minimum quantity of the key ingredient;

(e) preparing algorithms of compilations of stored data corresponding to historic data showing effects of temperature, time, moisture content, pH, and other variable conditions on physical properties of said viscous substance;

(f) positioning the viscous substance within or upon a specific container or enclosure;

(g) embedding sensors in an interior mass of the viscous substance;

(h) obtaining periodic measurements, transmitted from the sensors, of the specific physical properties of the viscous substance, in sequential segments of time;

(i) accessing the previously-prepared algorithms for direct comparison with the periodic measurements obtained from the sensors and thereby converting the obtained measurements into a rendering of a stage, or quality, of the specific physical property of the viscous substance;

(j) transmitting a conversion of the quality of the specific physical property to a mobile phone, electronic storage device, or desktop computer of an end user;

(k) utilizing steps (e) through (j) to produce a more accurate and appropriate improved margin of safety requirement wherein the improved margin of safety requirement is less than the standard margin of safety requirement.

Thus, by lowering the margin of safety requirement (i.e., improved) to produce a batch of concrete, less key ingredient is utilized, a lower quantity of greenhouse gases is produced as it is directly proportional to the amount of the key ingredient utilized.

Similarly, by lowering the margin of safety requirement (i.e., improved) to produce a batch of concrete, less key ingredient is utilized, a cost benefit is realized in producing the batch due to the reduced quantity of the key ingredient. Thus, the benefit is a cost savings in the total production without affecting the quality of the finished product.

While the specification has been described in detail with respect to specific embodiments thereof, it will be appreciated that those skilled in the art, upon attaining an understanding of the foregoing, may readily conceive of alterations to, variations of, and equivalents to these embodiments.

What is claimed is:

1. A method for realizing a benefit by reducing an amount of at least one key ingredient by utilizing a process for determination, at any point in time, a quality or phase of a specific physical property of a viscous substance, as the substance progresses through a stages of a particular process, the method comprising:

(a) ascertaining a desired compressive strength requirement for a predetermined viscous substance in pounds per square inch ("psi") as a minimum required psi;

(b) calculating a standard margin of safety requirement of ten percent of said compressive strength requirement but wherein said standard margin of safety requirement is not less than 500 psi even if said compressive strength requirement is less than 5000 psi;

(c) ascertaining a minimum quantity of a key ingredient in said viscous substance based on a sum of said compressive strength and said standard margin of safety requirement;

(d) reviewing existing scientific tables to ascertain how much of a greenhouse gas is produced in creating a predetermined amount of said viscous substance based on said minimum quantity of said key ingredient;

(e) preparing algorithms of compilations of stored data corresponding to historic data showing effects of temperature, time, moisture content, pH, and other variable conditions on physical properties of said viscous substance;

(f) positioning said viscous substance within or upon a specific container or enclosure;

(g) embedding sensors in an interior mass of said viscous substance;

(h) obtaining periodic measurements, transmitted from said sensors, of said specific physical properties of said viscous substance, in sequential segments of time;

(i) accessing said previously-prepared algorithms for direct comparison with said periodic measurements obtained from said sensors and thereby converting said obtained measurements into a rendering of a stage, or quality, of said specific physical property of said viscous substance;

(j) transmitting a conversion of said quality of said specific physical property to a mobile phone, electronic storage device, or desktop computer of an end user;

(k) utilizing steps (e) through (j) to produce a more accurate and appropriate improved margin of safety requirement wherein said improved margin of safety requirement is less than said standard margin of safety requirement.

2. The method of claim 1, further comprising the step of: using said improved margin of safety requirement to produce a batch of concrete such that an improved minimum quantity of said key ingredient is utilized wherein said improved minimum quantity is a sum of said compressive strength and said improved margin of safety requirement, and wherein a lower quantity of greenhouse gases is produced in producing said batch due to said improved quantity of said key ingredient compared with said minimum quantity as production of greenhouse gases is directly proportional to an amount of said key ingredient utilized, thus wherein said benefit is a reduction in production of greenhouse gases.

3. The method of claim 1, further comprising the step of:
using said improved margin of safety requirement to produce a batch of concrete such that an improved minimum quantity of said key ingredient is utilized wherein said improved minimum quantity is a sum of said compressive strength and said improved margin of safety requirement, and wherein a cost benefit is realized in producing said batch due to said improved quantity of said key ingredient compared with said minimum quantity as a total production cost of concrete is directly proportional to an amount of said key ingredient utilized, thus wherein said benefit is a cost savings in said total production.

4. The method of claim 1, wherein said viscous substance is selected from the group consisting of concrete slurry and asphalt.

5. The method of claim 1, wherein said viscous substance is being transported through a pipeline or conduit.

6. A method for realizing a benefit by reducing an amount of at least one key ingredient by utilizing a process for determination, at any point in time, a quality or phase of a specific physical property of a viscous substance, as the substance progresses through a stages of a particular process, the method comprising:
(a) ascertaining a desired compressive strength requirement for a predetermined viscous substance in pounds per square inch ("psi") as a minimum required psi;
(b) calculating a standard margin of safety requirement of ten percent of said compressive strength requirement but wherein said standard margin of safety requirement is not less than 500 psi even if said compressive strength requirement is less than 5000 psi;
(c) ascertaining a minimum quantity of a key ingredient in said viscous substance based on a sum of said compressive strength and said standard margin of safety requirement;
(d) reviewing existing scientific tables to ascertain how much of a greenhouse gas is produced in creating a predetermined amount of said viscous substance based on said minimum quantity of said key ingredient;
(e) preparing algorithms of compilations of stored data corresponding to historic data showing effects of temperature, time, moisture content, pH, and other variable conditions on physical properties of said viscous substance;
(f) positioning said viscous substance within or upon a specific container or enclosure;
(g) embedding sensors in an interior mass of said viscous substance;
(h) obtaining periodic measurements, transmitted from said sensors, of said specific physical properties of said viscous substance, in sequential segments of time;
(i) accessing said previously-prepared algorithms for direct comparison with said periodic measurements obtained from said sensors and thereby converting said obtained measurements into a rendering of a stage, or quality, of said specific physical property of said viscous substance;
(j) transmitting a conversion of said quality of said specific physical property to a mobile phone, electronic storage device, or desktop computer of an end user;
(k) utilizing steps (e) through (j) to produce a more accurate and appropriate improved margin of safety requirement wherein said improved margin of safety requirement is less than said standard margin of safety requirement; and using said improved margin of safety requirement to produce a batch of concrete such that an improved minimum quantity of said key ingredient is utilized wherein said improved minimum quantity is a sum of said compressive strength and said improved margin of safety requirement, and wherein a lower quantity of greenhouse gases is produced in producing said batch due to said improved quantity of said key ingredient compared with said minimum quantity as production of greenhouse gases is directly proportional to an amount of said key ingredient utilized, thus wherein said benefit is a reduction in production of greenhouse gases.

7. The method of claim 6, wherein said viscous substance is selected from the group consisting of concrete slurry and asphalt.

8. The method of claim 6, wherein said viscous substance is being transported through a pipeline or conduit.

9. A method for realizing a benefit by reducing an amount of at least one key ingredient by utilizing a process for determination, at any point in time, a quality or phase of a specific physical property of a viscous substance, as the substance progresses through a stages of a particular process, the method comprising:
(a) ascertaining a desired compressive strength requirement for a predetermined viscous substance in pounds per square inch ("psi") as a minimum required psi;
(b) calculating a standard margin of safety requirement of ten percent of said compressive strength requirement but wherein said standard margin of safety requirement is not less than 500 psi even if said compressive strength requirement is less than 5000 psi;
(c) ascertaining a minimum quantity of a key ingredient in said viscous substance based on a sum of said compressive strength and said standard margin of safety requirement;
(d) reviewing existing scientific tables to ascertain how much of a greenhouse gas is produced in creating a predetermined amount of said viscous substance based on said minimum quantity of said key ingredient;
(e) preparing algorithms of compilations of stored data corresponding to historic data showing effects of temperature, time, moisture content, pH, and other variable conditions on physical properties of said viscous substance;
(f) positioning said viscous substance within or upon a specific container or enclosure;
(g) embedding sensors in an interior mass of said viscous substance;
(h) obtaining periodic measurements, transmitted from said sensors, of said specific physical properties of said viscous substance, in sequential segments of time;
(i) accessing said previously-prepared algorithms for direct comparison with said periodic measurements obtained from said sensors and thereby converting said obtained measurements into a rendering of a stage, or quality, of said specific physical property of said viscous substance;

(j) transmitting a conversion of said quality of said specific physical property to a mobile phone, electronic storage device, or desktop computer of an end user;

(k) utilizing steps (e) through (j) to produce a more accurate and appropriate improved margin of safety requirement wherein said improved margin of safety requirement is less than said standard margin of safety requirement; and using said improved margin of safety requirement to produce a batch of concrete such that an improved minimum quantity of said key ingredient is utilized wherein said improved minimum quantity is a sum of said compressive strength and said improved margin of safety requirement, and wherein a cost benefit is realized in producing said batch due to said improved quantity of said key ingredient compared with said minimum quantity as a total production cost of concrete is directly proportional to an amount of said key ingredient utilized, thus wherein said benefit is a cost savings in said total production.

10. The method of claim 9, wherein said viscous substance is selected from the group consisting of concrete slurry and asphalt.

11. The method of claim 9, wherein said viscous substance is being transported through a pipeline or conduit.

* * * * *